United States Patent [19]

Schainholz

[11] Patent Number: 4,806,100
[45] Date of Patent: Feb. 21, 1989

[54] MANDIBLE MANIPULATION DEVICE

[76] Inventor: Herbert Schainholz, 316 Locust St., Teaneck, N.J. 07006

[21] Appl. No.: 132,815
[22] Filed: Dec. 14, 1987
[51] Int. Cl.$^4$ .............................................. A61C 19/04
[52] U.S. Cl. ...................................................... 433/73
[58] Field of Search ...................... 433/73, 68, 136, 39

[56] References Cited

U.S. PATENT DOCUMENTS

| 757,133 | 4/1904 | Marshall | 433/68 |
| 2,461,207 | 2/1949 | Frowine | 433/73 |

Primary Examiner—Robert Peshock
Attorney, Agent, or Firm—McAulay, Fields, Fisher, Goldstein & Nissen

[57] ABSTRACT

The present invention provides a mandible manipulation device that, in a preferred embodiment, consists of a frame having a pair of elongated, lengthwise members that are adjustably connected to a transverse member. In the preferred embodiment, an impression tray, that is provided to hold a mouthpiece against the teeth of the mandible, is connected to one of the lengthwise members. A mandible support, to support the underside of the mandible, is connected to the other of the lengthwise members. The lengthwise members are adapted for adjustable movement to a fixed position in which the mandible is held between the mouthpiece and the mandible support. The mandible can thereafter, be manipulated by manipulation of the lengthwise members.

16 Claims, 2 Drawing Sheets

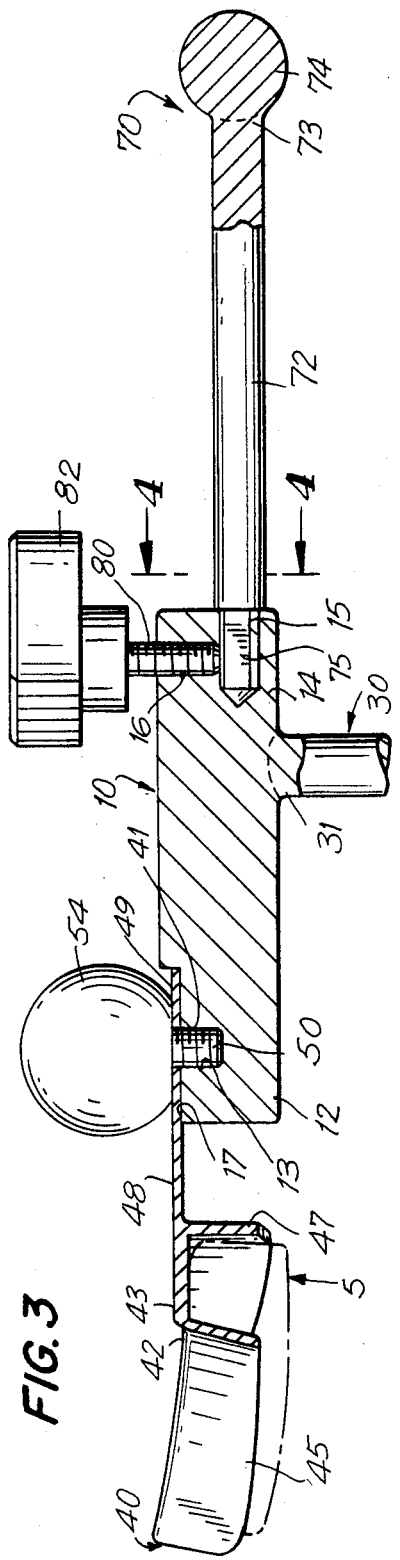
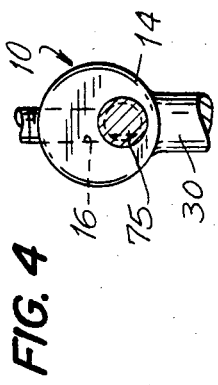
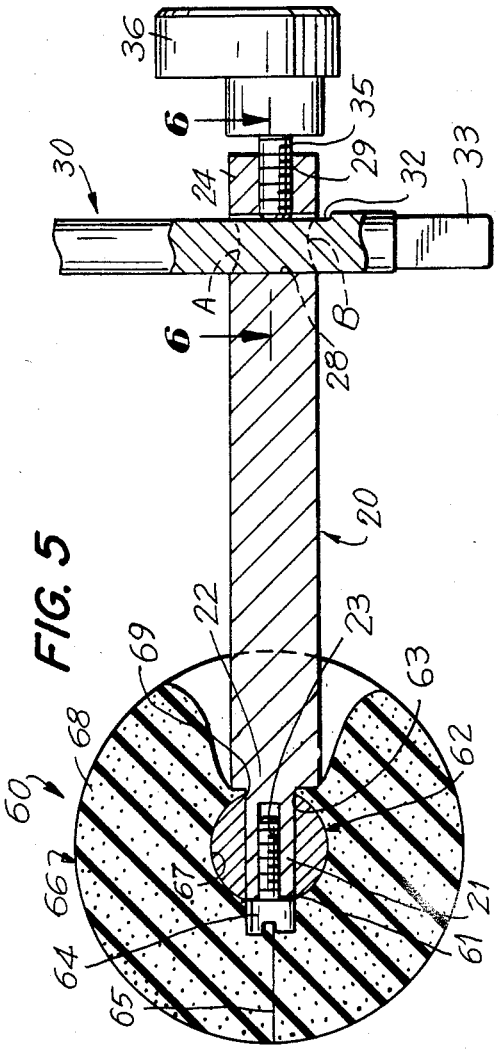

MANDIBLE MANIPULATION DEVICE

FIELD OF THE INVENTION

The present invention relates to devices for manipulating the mandible and more particularly, the present invention relates to a device for manipulating the mandible wherein the mandible is held by the device.

BACKGROUND OF THE INVENTION

As is well known in the art, various medical and dental procedures require the mandible to be manipulated and held in one position. When the mandible is manipulated, the medical or dental practitioner often has to insert his or her fingers into the mouth causing discomfort to the patient. Even when the patient is anesthetized, this manipulation can become particularly burden-some during surgical procedures involving the mandible and/or the temporomandibular joint because during such procedures, the mandible is manipulated solely by hand. For instance, when arthroscopy is performed on the temporomandibular joint, prior to the actual surgery, the mandible is moved and positioned in order to allow the surgeon to visually inspect the joint for diagnostic purposes. Thereafter, the mandible is held in a stable position in order to permit the surgeon to perform and complete the surgery. As can be appreciated, such surgery is complicated by the fact that the mandible is positioned and held by an assistant under the direction of the surgeon. The present invention simplifies such surgery by providing a mandible manipulation device that can act as a surgical clamp for the mandible. In a preferred embodiment of the present invention, the mandible is held between a dental impression or a rubber mouthpiece, retained in an impression tray, and a padded mandible support. The tray and support are attached to an elongated frame that is adjustable to permit the impression tray and dental impression to be inserted into the mouth and the mandible support to be positioned under the mandible. The surgeon can manipulate the frame in order to view the temporomandibular joint during the inspection and diagnostic phase of the surgery. Thereafter, during the actual surgery, the device can be attached to an instrument support to hold the mandible in place. Thus, when a device in accordance with the present invention is used for such surgery, an assistant is not required to manipulate and hold the mandible. As can be appreciated by those skilled in the art, the present invention is also useful as a surgical clamp for the mandible during arthroscopy of the temporomandibular joint. Moreover, when used in a dental procedure, the mandible, being held within the device, can be manipulated without the practitioner inserting his or her hands into the mouth and causing the patient further pain and discomfort.

The present invention, although described above as a surgical clamp, is not intended to be so limited in its application. In fact, the present invention has application to any therapeutic procedure in which the mandible is required to be manipulated. For instance, the present invention could be used, after temporomandibular joint surgery, to operate the joint in a systematic fashion as physical therapy for the joint.

SUMMARY OF THE INVENTION

The present invention provides a mandible manipulation device. The device includes, in a basic for, an elongated frame, means for holding a dental impression against the teeth of the mandible of a patient and means, located directly opposite to the dental impression holding means, for supporting the underside of the mandible. The frame has a pair of elongated, lengthwise members, located in one plane, that are adapted for adjustable movement to fixed positions towards and away from one another. The frame also has means, spaced from one side of the frame, for adjustably connecting the lengthwise members to one another in the fixed positions. The dental impression holding means include means for connecting the dental impression, to one end of one of the lengthwise members, on the one side of the frame. The mandible supporting means are connected to one end of the other of the lengthwise members also, on the one side of the frame. The lengthwise members are thus operable for movement to a fixed position in which the mandible is securely held between the dental impression and the mandible supporting means. The mandible, thereafter, can be manipulated by changing the orientation of the frame.

DESCRIPTION OF THE DRAWING

In the accompanying drawings:

FIG. 3 is an enlarged, fragmentary cross-sectional view taken lines 3—3 of FIG. 1 with a dental impression shown in lines.

FIG. 4 is an enlarged, fragmentary cross-sectional view taken along lines 4—4 of FIG. 3.

FIG. 5 is an enlarged, fragmentary cross-sectional view taken along lines 5—5 of FIG. 1.

FIG. 6 is an enlarged, fragmentary cross-sectional view taken along lines 6—6 of FIG. 5.

DETAILED DESCRIPTION OF THE INVENTION

Figure 1:
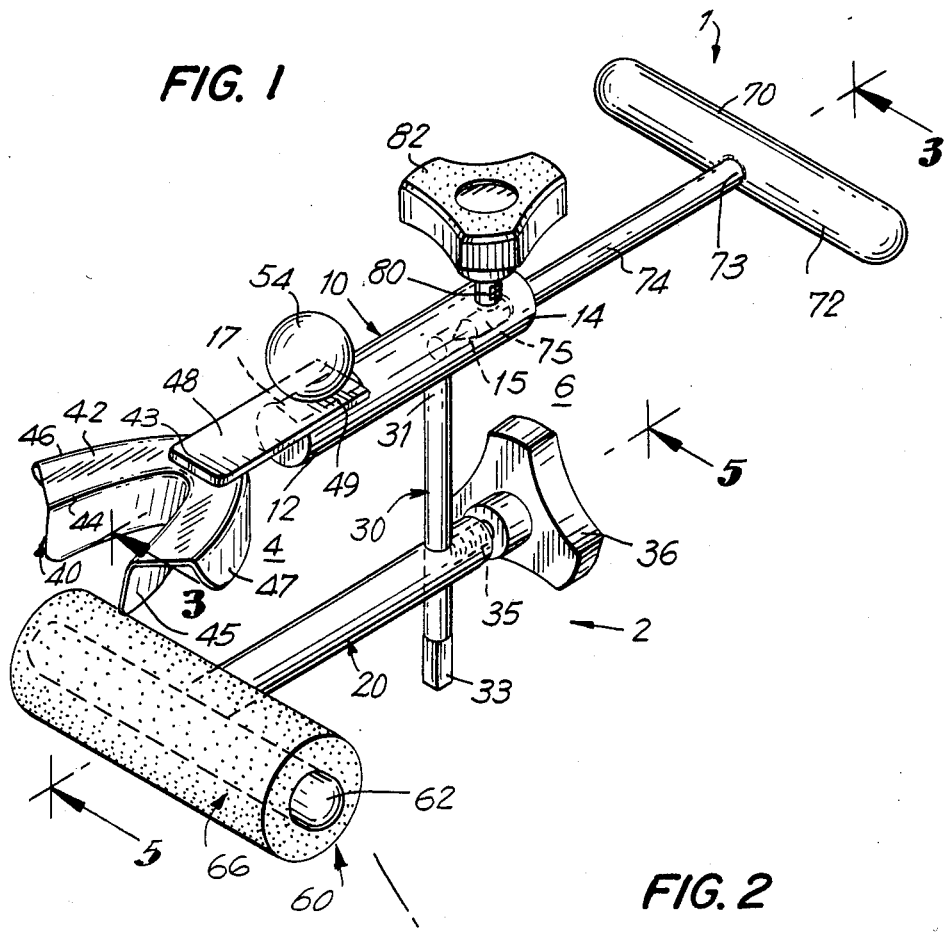
FIG. 1 is a perspective view of the mandible manipulation device of the present invention.
Figure 2:
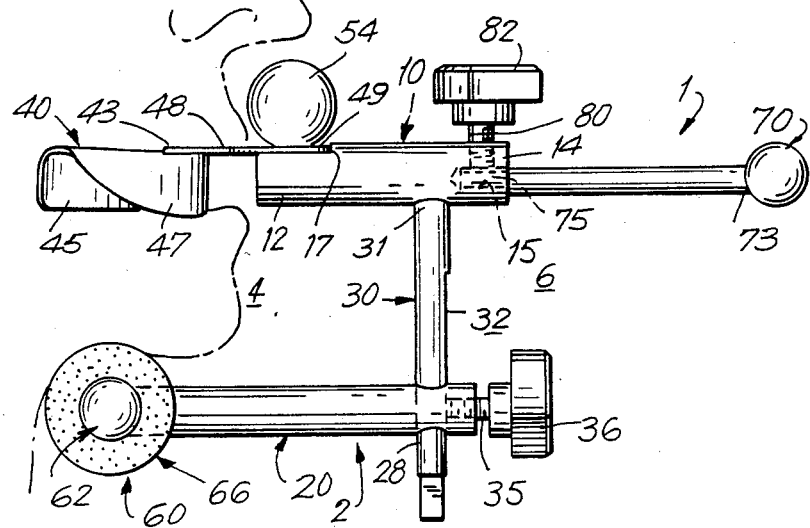
FIG. 2 is a left side elevational view of the mandible manipulation device of the present invention within the mouth of a patient shown in phantom lines.

With reference now to FIGS. 1, 2 and 3 the mandible manipulation device 1 of the present invention can include a frame 2 having a pair of lengthwise members 10 and 20 that are preferably adjustably connected to one another by being adjustably connected to a transverse member 30. As illustrated, the adjustable connection can preferably be accomplished, in part, by selectively locking the lengthwise member 20 against the transverse member 30 through the use of a first set screw member 35. In a preferred embodiment, a mouthpiece or other dental impression 5, known well in the art, can be held in place by an impression tray 40, connected to the lengthwise member 10. The underside of the mandible is preferably supported by a mandible support 60 connected to lengthwise member 20. In practice, the lengthwise members 10 and 20 would be adjusted to a fixed position, relative to one another, wherein the mandible is securely held between the dental impression 5 and the mandible support 60. In accordance with the present invention, a removable handle 70 can be provided for manipulating the orientation of the lengthwise members 10 and 20, which in turn, positions the mandible, and in the case of temporomandibular joint surgery, the temporomandibular joint.

Having briefly described the subject invention, a more detailed description begins with the description of one of the lengthwise members 10. Lengthwise member 10 can preferably have an elongated configuration that can be in the form of a cylindrical rod. Lengthwise member 10 can be provided with a first transversely oriented threaded bore 13, located in end 12, that can be used with a threaded connection member 50 to connect an impression tray 40 that retains a mouthpiece or other dental impression 5. Lengthwise member 10 can also be provided with an axially oriented, socket-like bore 15 located in its other end 14. Bore 15 is sized to slidably receive a pin 75 of the handle member 70. A second transversely oriented threaded bore 16 can also be provided in the end of lengthwise member 10. The second transversely oriented threaded bore 16 intersects the socket-like bore 15 and is used with a second set screw member 80 for connection of the handle 70.

With reference to FIGS. 2, 5 and 6, the other lengthwise member 20 can be an elongated member having the configuration of a cylindrical rod. The lengthwise members 10 and 20 are located in one plane, preferably parallel to one another, and are adapted for adjustable movement to fixed positions towards and away from one another. The lengthwise members 10 and 20 are preferably connected to the elongated transverse member 30. Transverse member 30 is spaced from side 4 of the frame 2 and is oriented at right angles to the lengthwise members 10 and 20. The connection of the lengthwise members 10 and 20 to the transverse member 30 is an adjustable connection that permits the lengthwise members 10 and 20 to be adjusted to fixed positions towards and away from one another. In the illustrated, preferred embodiment, this adjustable connection includes the transverse member 30 being connected, at end 31, to the lengthwise member 10. The lengthwise member 20, is provided with a transverse bore 28 communicating between opposite points, illustrated by A and B, of the outer surface thereof. The transverse bore 28 is sized and oriented to slidably receive the transverse member 30. An axially oriented threaded bore 29 can be provided, in the end 24, that intersects the transverse bore 28. In the preferred embodiment, the transverse member 30 can also have the configuration of a cylindrical rod. Bore 28 therefore, preferably has a circular, transverse cross-section. As mentioned previously, the first set screw member 35 is provided to selectively lock the lengthwise member 20 in place against the transverse member 30. To this end, the first set screw member 35 is configured to threadably engage within the bore 29 and bear against the transverse member 30 within transverse bore 28. As illustrated, the first set screw member 35 can be provided, at one end, with an enlarged knob 36 to aid in threading member 35 through bore 29.

In the preferred embodiment, the transverse member 30 can be provided with an elongated, flat bearing surface 32 extending along the length of transverse member 30, between the ends 31 and 33 thereof. When the set screw member 35 is threaded into the bore 29, the threaded member 35 bears against the bearing surface 32. The bearing surface 32 thereby prevents rotational movement of the lengthwise members 10 and 20 relative to one another. As illustrated, the transverse member 30 extends through the bore 28 with the end 33 projecting from the bore 28. The end 33 of transverse member 30 can have a square, transverse cross section that is operable to fit within the socket of an instrument support known well in the art. Such an instrument support, which would be secured to a patient support, could be used to support the device 1 in a stable position and hence, the head and temporomandibular joint in a stable position during arthroplasty of the temporomandibular joint. An example of an instrument support is the flexible instrument holder and positioner illustrated in U.S. Pat. No. Des. 239,131, which is hereby incorporated by reference.

Referring now to FIGS. 1 and 3, means are provided to hold a dental impression 5, such as a football-type mouthpiece, that can be the preferred impression tray 40. The impression tray 40 can have a horseshoe-like basewall 42 and a pair of inner and outer arcuate edges 44 and 46 spaced apart from another. As illustrated, an inner sidewall 45, can be provided, that is integrally formed and downwardly depends from the inner arcuate edge 44. Additionally, an outer sidewall 47 can be provided that is integrally formed and downwardly depends from the outer arcuate edge 46. In practice, a mouthpiece, known well in the art, could be retained or held between the flanges 45 and 47 and the basewall 46. The mouthpiece is used to bear against the teeth and hence the mandible of the patient. The impression tray 40 is connected to end 12 of the lengthwise member 10 by the preferred means of a planar, elongated connection element 48 that is connected at end 43 to the apex of the basewall 42. The other end 49, of the connection element 48, can preferably be provided with a hole 41. The connection element 48 can be connected to the end 12 of the lengthwise member 10 by the preferred means of a threaded connection member 50. As illustrated the end 12 of the lengthwise member 10 preferably has a flat, rectangular, shoulder-like recess 17. Recess 17 extends in a direction parallel to the length of the lengthwise member 10. The first transversely oriented threaded bore 13 is preferably defined at the recess 17. Additionally, the hole 41 is located on the end 49 of connection element 48 so as to be in alignment with bore 13 when connection element 48 is placed upon recess 17. Threaded member 50, preferably has, at one end, an enlarged knob 54. The threaded member 50 is configured, to extend through hole 41, to threadably engage within the bore 13 and to be tightened so that knob 54 bears against the connection element 48.

The threaded connection of the impression tray 40 to the lengthwise member 10 is preferred in that it is advantageous for the impression tray 40 to be operable for easy removal from the lengthwise member 10 for cleaning and sterilization. It is understood however, that the preferred impression tray 40 could be connected to end 12 by permanent means, such as welding. Additionally, the connection element 48 is sized such that the apex of the basewall 42 and hence, the impression tray 40 is spaced from the end 12 of the lengthwise member 10. This arrangement is preferred so that the end 12 of the lengthwise member 10 is not within the mouth of the patient when the device 1 is in use.

With reference again to FIGS. 2 and 5, means are provided for supporting the underside of the mandible, such as the illustrated mandible support 60. The mandible support 60 can include an elongated cross member 62 that is centrally connected to end 22 of the lengthwise member 20, preferably at right angles. As illustrated, a pair of opposed holes 61 and 63 are provided in the outer circumference of cross member 62. The lengthwise member 20 has an axially extending element 21, that extends from end 22 and that is sized to extend into hole 63. The element 21 has a threaded bore 23. A threaded fastener 64, is configured to be extended into bore 61 and threaded into the bore 23 of the element 21 to connect the mandible support 60, by cross member 62, to the lengthwise member 20. The mandible support can also include a tubular padded member 66 having an inner periphery 67 that is sized to tightly receive the cross member 62. Padded member 66 can also be provided with a radial aperture 69 that communicates between the inner periphery 67 and an outer periphery 68 of the padded member 66. Aperture 69 is centrally located on padded member 66 and is sized to receive element 21. Slit 65 is provided in padded member 66 for removal of the fastener 64. In this regard, fastener 64 can be provided with a socket configured to receive a hex wrench through slit 65. As could be appreciated, cross member 62 could be permanently attached to lengthwise member 22. In such case, padded member 66 would have to be provided with a lengthwise slit to permit removal for replacement and cleaning. Padded member 66 can be fabricated from foam rubber or other resilient cushioning material.

With particular reference now to FIGS. 3 and 4, an optional removable handle 70 can be provided on the other side, illustrated by 6, of the frame 2, for added leverage for manipulating the orientation of the frame 2 and hence, the position of the mandible Handle 70 preferably includes a handgrip element 72 and a shank-like element 74. Element 74 is connected, at one of its ends 73, to the handgrip element 72. As previously discussed, the other ends of the shank-like element 74 can comprise a pin 75 that is configured to slidably fit within bore 15. As previously mentioned, the other end 14 of the lengthwise member 10 can be provided with a second transversely oriented threaded bore 16 that intersects the socket-like bore 1. A second set screw member 80 can be provided that is connected, at one end, to an enlarged knob 82. The set screw member 80 is threaded into bore 16 to bear against pin 75 when installed in bore 15. Threaded member 80 can be loosened by manipulation of knob 82 to permit removal of the handle 70 for cleaning and sterilization. It should also be pointed out that handle 70 would normally be removed after the surgeon has completed the manipulation of the mandible and the joint so as not to obstruct his or her movements and viewing area during the performance of the actual surgery. It is also understood that the embodiment of the present invention could be made without the handle 70. In such a case the surgeon would simply grasp the lengthwise members 10 and 20 for manipulation of the frame 1 and the position of the mandible.

It is understood that, alternately, a socket-like bore, such as illustrated at 15, could be provided in the lengthwise member 20 for connection of the handle 70. In such case, the transverse member 30 would be connected, at one end, to the lengthwise member 20 and the lengthwise member 10 would be provided with the transverse bore, such as illustrated at 28, to receive the transverse member 30. Additionally, the lengthwise member 10 would also be provided with an axially extending bore, such as illustrated at 29, to receive a set screw member, such as illustrated at 35, to lock the lengthwise member 10 in place against the transverse member 30.

Although the preferred, illustrated embodiment has been described relative to a device that can be advantageously used for temporomandibular joint surgery, as stated previously, the present invention has application to any therapeutic need wherein the mandible is held and manipulated during such therapy. For instance, as would occur to one skilled in the art, the device 1 can be utilized for therapeutic purposes without the handle 70. In such case, the member 10 could be connected at end 14 to an automated machine for the systematic manipulation of the mandible of the patient for physical therapy of the temporomandibular joint.

With reference again to FIGS. 1 and 2, it can be seen that when the preferred mandible support 60 is used with the tray 40, the support 60 must support the mandible directly opposite to the tray 40 in order for device 1 to securely grip the mandible. To this end, the lengthwise member 20 is sized, relative to lengthwise member 10, such that the distance as measured between the transverse member 30 and the mandible support 60 is equal to the distance between a central point of the base wall 42 and the transverse member 30. As a result, the mandible support 60 is located directly opposite or below the preferred impression tray 40 when device 1 is in use. Additionally, in order to permit the device 1 to be compact, the lengthwise member 10 is shorter than the lengthwise member 20.

While specific embodiments of the invention have been shown, the invention should not be considered as so limited, but only as limited as set forth in the appended claims.

I claim:
1. A mandible manipulation device including:
an elongated frame having,
a pair of elongated, lengthwise members, located in one plane adapted for adjustable movement to fixed positions towards and away from one another, and
means, spaced from one side of said frame, for adjustably connecting said lengthwise members to one another in said fixed positions;
means for holding a dental impression against the teeth of the mandible of a patient and for connecting said dental impression to one end of one of said lengthwise members, on said one side of said frame; and
means, located directly opposite to said dental impression holding means, connected to one end of the other of said lengthwise numbers, on said one side of said frame, at right angles to said one plane of said lengthwise member and having a length at least as wide as said mandible for supporting the underside of said mandible, whereby said lengthwise members are operable for movement to a said fixed position in which said mandible is securely held between said dental impression and said mandible supporting means and said mandible is operable to be manipulated by changing the orientation of said frame.

2. The mandible manipulation device of claim 1 further including:
a handle; and
means for removably connecting said handle to the other side said frame.

3. The mandible manipulation device of claim 1 wherein:
said lengthwise members are parallel to one another; and
said adjustable connection means include,
an elongated transverse member, spaced from said one side of said frame, oriented at right angles to said lengthwise members, and means for adjustably connecting said lengthwise members to said transverse member in said fixed positions.

4. The mandible manipulation device of claim 3 wherein said adjustable connection means includes:
said transverse member being connected, at one end, to said one lengthwise member;
said other lengthwise member having,
a transverse bore communicating between opposite points of the outer surface thereof, said transverse bore being sized and oriented to slidably receive said transverse member, and
an axially extending threaded bore located in the other end thereof, intersecting said transverse bore;
said transverse member extending through said transverse bore; and
a first set screw member that is operable to be threaded into said axially extending threaded bore and bear against said transverse member to lock said other lengthwise member in place against said transverse member.

5. The mandible manipulation device of claim 4 wherein said transverse member has a flat elongated bearing surface extending along the length of said transverse member between the ends thereof, said bearing surface located on said transverse member such that said first screw member bears against bearing surface to prevent the relative rotation of said lengthwise members with respect to one another.

6. The mandible manipulation device of claim 5 wherein the other end of said transverse member has a square transverse cross section that is operable to be located in a socket of an instrument support.

7. The mandible manipulation device of claim 1 wherein said dental impression holding and connection means includes:
an impression tray comprising,
an arcuate, planar basewall having,
an apex located adjacent to said one end of said one lengthwise member,
an inner arcuate edge, and
an outer arcuate edge spaced from said inner arcuate edge,
an outer arcuate sidewall integrally formed and depending from said outer arcuate edge,
an inner arcuate sidewall integrally formed and depending from said inner arcuate edge; and
means for connecting said impression tray, at said apex of said basewall, to said one end of said one lengthwise member, whereby said dental impression can be retained against said basewall and between said inner and outer arcuate sidewalls.

8. The mandible manipulation device of claim 1 wherein said mandible supporting means comprises a mandible support that includes:
an elongated cross member; and
an elongated, resilient padded member of tubular configuration having,
an inner periphery sized to receive said cross member, and
an outer periphery that bears against said mandible of said patient, said padded member being installed on said cross member and said mandible support being centrally connected to said one end of said other lengthwise member at right angles.

9. The mandible manipulation device of claim 2 wherein:

said handle has,
an elongated handgrip element, and
an elongated shank-like element connected, at one end, to said handgrip element; and
said handle connection means include means for connecting the other end of said shank-like element to said one end of said one lengthwise member.

10. The mandible manipulation device of claim 4 wherein said dental impression holding and connection means includes:
an impression tray comprising,
an arcuate planar basewall having,
an apex located adjacent to said one end of said one lengthwise member,
an inner arcuate edge, and,
an outer arcuate edge spaced from said inner arcuate edge,
an outer arcuate sidewall integrally formed and depending from said outer arcuate edge,
an inner arcuate sidewall integrally formed and depending from said inner arcuate edge: and
means for connecting said impression tray, at said apex of said basewall, to the said one end of said one lengthwise member, whereby said dental impression can be retained against said basewall and between said inner and outer sidewalls.

11. The mandible manipulation device of claim 10 wherein:
said mandible supporting means comprises a mandible support, including,
an elongated cross member; and
an elongated resilient padded member of tubular configuration having,
an inner periphery sized to receive said cross member; and
an outer periphery that bears against said chin of said patient, said padded member being installed on said cross member and said mandible support being centrally connected to said one end of said other lengthwise member at right angles; and
said other lengthwise member is sized such that the distance between said mandible support and said transverse member is equal to the distance between a central point of said basewall and said transverse member.

12. The mandible manipulation device of claim 11 further including;
a handle having,
an elongated handgrip element, and
an elongated shank-like element connected at one end to said handgrip element; and
means for connecting said handle, at the other end of said shank-like element, to the said other end of said one lengthwise member.

13. The mandible manipulation device of claim 12 wherein:
said one end of said one lengthwise member has, a flat rectangular shoulder-like recess that extends in a direction parallel with the length of said lengthwise member, and a first transversely oriented threaded bore defined at said recess; and
said mouthpiece holder connection means includes,
a planar, rectangular connection element connected, at one end, to said apex of said basewall and configured, at the other end, to fit within said recess, said other end of said connection element having a hole that is located so as to be operable to be brought into alignment with said first threaded bore, and a threaded connection member, having, at one end, an enlarged knob, said threaded connection member being operable to be extended to said hole and threaded into said first threaded bore with said knob bearing against said connection element.

14. The mandible manipulation device of claim 13 wherein:

said other end of said shank-like element comprises a pin;

said other end of said one lengthwise member has, an axially extending socket-like bore sized to receive said pin, and a second transversely oriented threaded bore that intersects said socket-like bore; and said handle connection means includes a second set screw member that is operable to be threaded into said second threaded bore and bear against said pin when said pin is inserted into said socket-like bore.

15. The mandible manipulation device of claim 14 wherein said transverse member has a flat elongated bearing surface extending along the length of said transverse member between the ends thereof, said bearing surface located on said transverse member such that said first set screw member bears against said bearing surface to prevent the relative rotation of said lengthwise members with respect to one another.

16. The mandible manipulation device of claim 15 wherein the other end of said transverse member has a square transverse cross-section that is operable to be located in a socket of an instrument support.

* * * * *